(12) United States Patent
Masaki et al.

(10) Patent No.: US 8,617,060 B2
(45) Date of Patent: Dec. 31, 2013

(54) ENDOSCOPE LIGHT SOURCE APPARATUS AND ENDOSCOPE SYSTEM

(71) Applicant: Olympus Medical Systems Corp., Tokyo (JP)

(72) Inventors: Takahiro Masaki, Kawasaki (JP); Kyosuke Mizuno, Hachioji (JP); Rihito Ishikawa, Hino (JP); Tomoya Takahashi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/652,796

(22) Filed: Oct. 16, 2012

(65) Prior Publication Data

US 2013/0109921 A1    May 2, 2013

Related U.S. Application Data

(63) Continuation of application No. PCT/JP2011/065983, filed on Jul. 13, 2011.

(30) Foreign Application Priority Data

Jul. 14, 2010    (JP) .................................. 2010-159953

(51) Int. Cl.
*A61B 1/06*    (2006.01)
(52) U.S. Cl.
CPC ............. *A61B 1/0646* (2013.01); *A61B 1/0669* (2013.01)
USPC ............................ 600/181; 600/178; 362/574
(58) Field of Classification Search
CPC ... A61B 1/0061; A61B 1/0669; A61B 1/0646

USPC .................... 600/178, 181; 362/574, 280, 282
See application file for complete search history.

(56) References Cited

U.S. PATENT DOCUMENTS

| 4,924,856 | A | 5/1990 | Noguchi |
| 4,983,019 | A | 1/1991 | Ikuno et al. |
| 5,007,408 | A | 4/1991 | Ieoka |
| 7,070,560 | B2 * | 7/2006 | Takahashi ..................... 600/178 |
| 8,066,409 | B2 * | 11/2011 | Toriyama et al. ............. 362/293 |

(Continued)

FOREIGN PATENT DOCUMENTS

| EP | 2 301 420 A1 | 3/2011 |
| JP | 01-170436 | 7/1989 |

(Continued)

*Primary Examiner* — John P Leubecker
(74) *Attorney, Agent, or Firm* — Scully, Scott, Murphy & Presser, P.C.

(57) ABSTRACT

An endoscope light source apparatus includes a turret provided with a first optical filter and a second optical filter for transmitting an illuminating light, an instruction section in which an operation instruction of the turret is inputted, a drive section that drives the turret, a first detector that detects a position of the turret, a first detected portion for identifying a position of the first optical filter, a second detected portion for identifying a position of the second optical filter, a second detector that optically detects a position of the first or the second detected portion, and a turret control section that outputs a drive signal to the drive section to move the turret until the first or the second detected portion is detected by the second detector and stop the turret in response to the first or the second detected portion being detected.

6 Claims, 9 Drawing Sheets

(56) References Cited

U.S. PATENT DOCUMENTS

| | | | |
|---|---|---|---|
| 8,167,796 B2* | 5/2012 | Negishi | 600/181 |
| 2007/0010714 A1* | 1/2007 | Negishi | 600/180 |
| 2007/0100205 A1* | 5/2007 | Iriyama | 600/118 |
| 2007/0263406 A1* | 11/2007 | Negishi | 362/574 |
| 2009/0290374 A1* | 11/2009 | Tashiro et al. | 362/574 |

FOREIGN PATENT DOCUMENTS

| | | |
|---|---|---|
| JP | 01-217414 | 8/1989 |
| JP | 02-020816 | 1/1990 |
| JP | 03-021219 | 1/1991 |
| JP | 08-107879 | 4/1996 |
| JP | 09-197294 | 7/1997 |
| JP | 2001-343595 | 12/2001 |
| JP | 2002-153422 | 5/2002 |
| JP | 2004-261227 | 9/2004 |
| JP | 2007-014451 | 1/2007 |
| JP | 2007-190180 | 8/2007 |
| JP | 2007-229135 | 9/2007 |
| JP | 2008-029740 | 2/2008 |
| JP | 2009-189495 | 8/2009 |
| JP | 2009-297436 | 12/2009 |
| WO | WO 2004/073509 A1 | 9/2004 |
| WO | WO 2009/154028 A1 | 12/2009 |

* cited by examiner

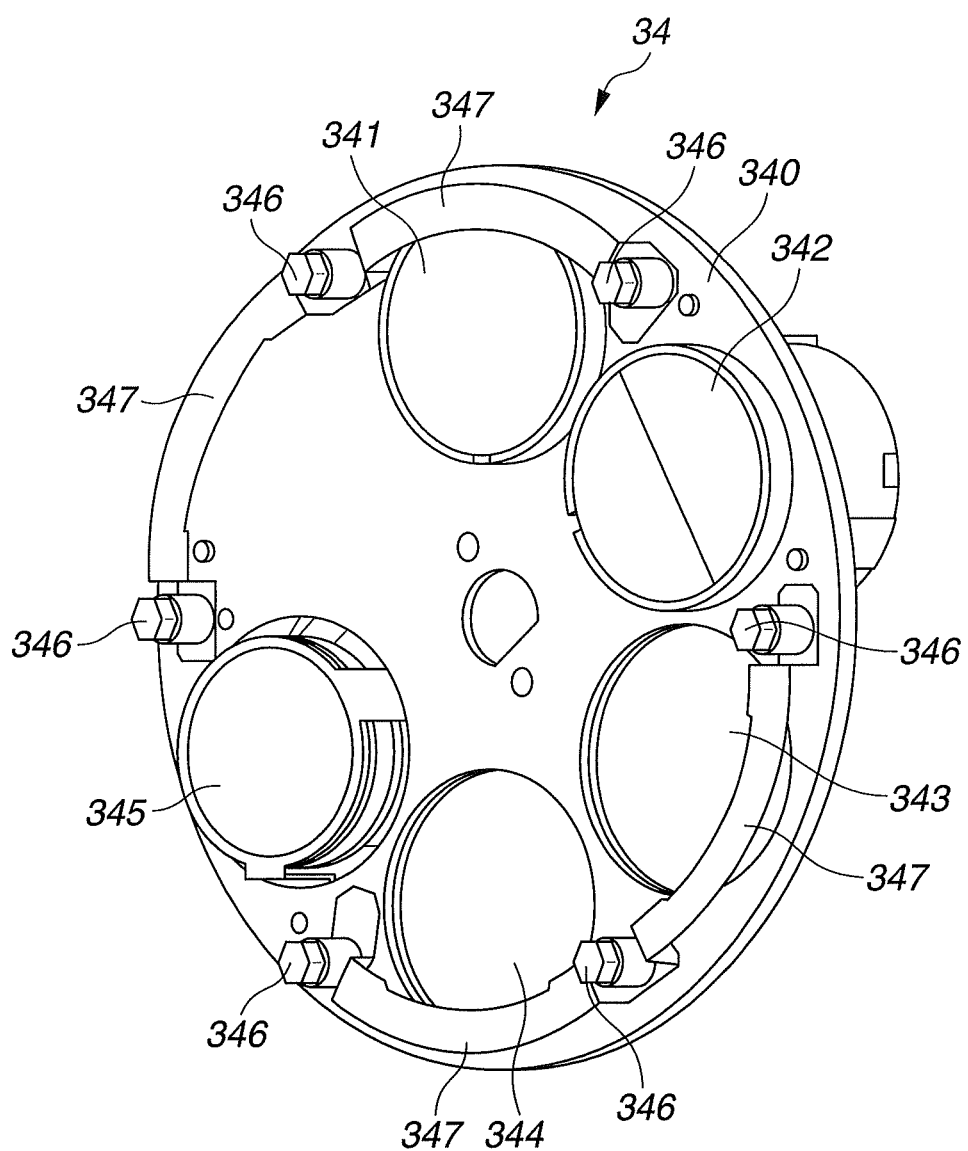

ENDOSCOPE LIGHT SOURCE APPARATUS AND ENDOSCOPE SYSTEM

CROSS REFERENCE TO RELATED APPLICATION

This application is a continuation application of PCT/JP2011/065983 filed on Jul. 13, 2011 and claims benefit of Japanese Application No. 2010-159953 filed in Japan on Jul. 14, 2010, the entire contents of which are incorporated herein by this reference.

BACKGROUND OF THE INVENTION

1. Field of the Invention

The present invention relates to an endoscope light source apparatus and an endoscope system, and more particularly to an endoscope light source apparatus that controls a turret provided with an optical filter for transmitting an illuminating light, and an endoscope system that picks up an image of an object by the illuminating light that passes through the turret.

2. Description of the Related Art

When inspection/observation or treatment is performed with use of an endoscope, a light source apparatus that emits an illuminating light, a video processor that processes an endoscopic image of an inspected site picked up by an image pickup device at an endoscope distal end, and a monitor that displays the processed endoscopic image are needed.

In a conventional light source apparatus for an endoscope, a plurality of filters are prepared and selection is made from the filters for use to adjust a light amount, a color tone and the like to a proper light amount, a proper color tone and the like in accordance with a kind of a body cavity to be observed, exposure at a time of photographing, a light amount of a light source lamp and the like. Further, an emergency light which is used in place of the light source lamp when the light source lamp fails during use of the light source lamp is also prepared.

The various filters and the emergency light are disposed at a circumferential portion of a turret, which is rotatably provided, along a circumferential direction thereof. The above-described turret is rotated, whereby the various filters and the emergency light which are needed are located on an emission light path (refer to, for example, Japanese Patent Application Laid-Open Publication No. 2001-343595).

The conventional turret includes a motor for rotating the turret, and a potentiometer mounted to a rotary shaft to detect a rotational angle of the turret.

In order to locate the filter corresponding to a use purpose on the emission light path out of a plurality of filters on the turret, it is necessary to correctly match a center of the target filter with an optical axis of the emission light by rotating the turret by a required angle.

SUMMARY OF THE INVENTION

An endoscope light source apparatus of one aspect of the present invention includes a turret provided with a first optical filter and a second optical filter for transmitting an illuminating light, an instruction section in which an operation instruction of the turret is inputted, a drive section that drives the turret, a first detector that detects a position of the turret, a first detected portion for identifying a position of the first optical filter, a second detected portion for identifying a position of the second optical filter, a second detector that optically detects a position of the first or the second detected portion, and a turret control section that outputs a drive signal to the drive section to move the turret until the first or the second detected portion is detected by the second detector in order to position the optical filter designated in response to an input of the instruction section, after moving the turret to an inside of a first range detected by the first detector, in response to the input of the instruction section, and stop the turret in response to the first or the second detected portion being detected.

BRIEF DESCRIPTION OF THE DRAWINGS

FIG. 3B is a perspective view showing a structure of the turret at an exit side;

DETAILED DESCRIPTION OF THE PREFERRED EMBODIMENTS

Hereinafter, embodiments of the present invention will be described in detail with reference to the drawings.

Figure 1:
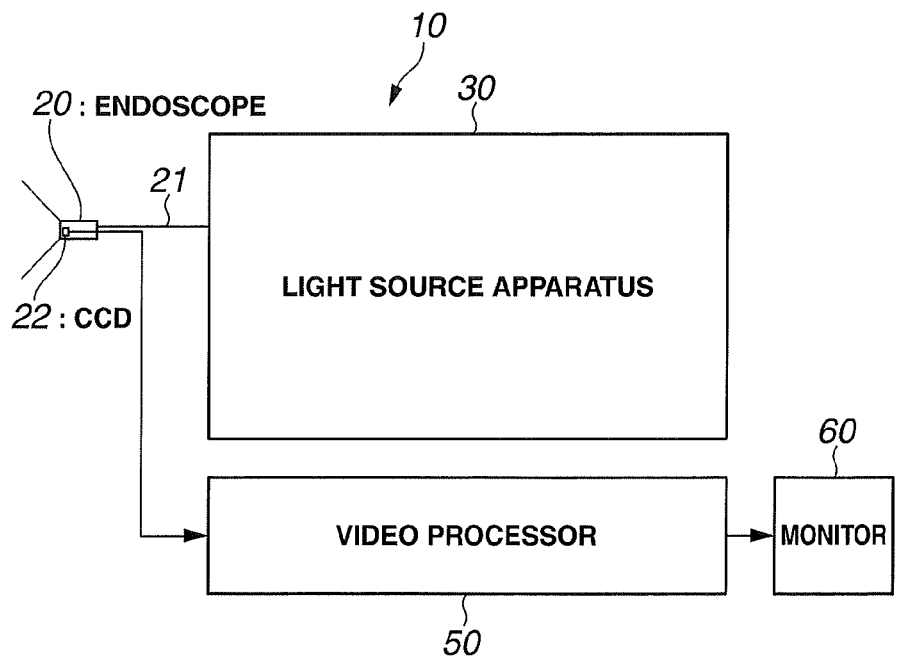
FIG. 1 is a block diagram showing an endoscope system according to the present invention.

FIG. 1 is a block diagram showing an endoscope system according to the present invention.

In FIG. 1, an endoscope system 10 includes an endoscope 20 that includes a light guide 21 that guides an illuminating light to a distal end portion and a CCD 22 as an image pickup device that performs image pickup of a subject, a light source apparatus 30 that emits light to the light guide that supplies the illuminating light to an endoscope distal end portion, a video processor 50 that processes an endoscope image of an inspected site that is picked up by the CCD 22 at the endoscope distal end portion, and a monitor 60 that displays the processed endoscopic image.

First Embodiment

Figure 2:
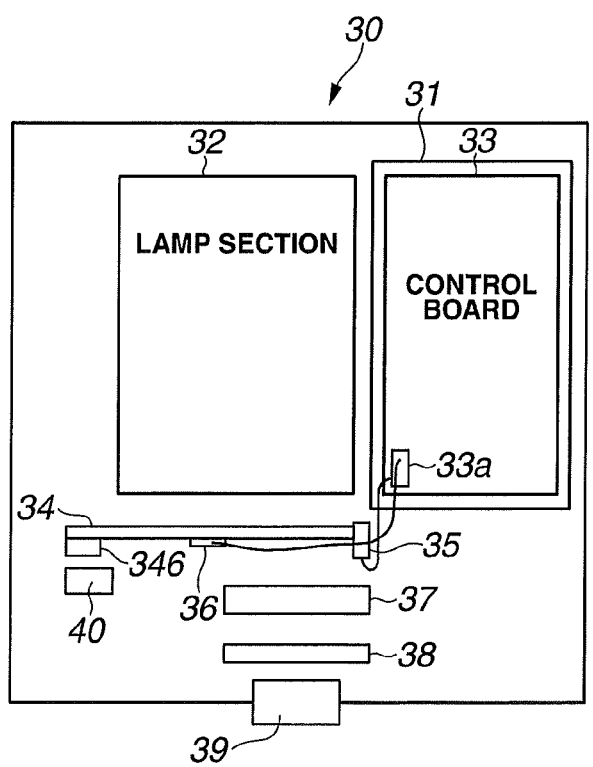
FIG. 2 is a plan view showing a structure of an endoscope light source apparatus interior of a first embodiment of the present invention.

FIG. 2 is a plan view showing a structure of an endoscope light source apparatus interior of a first embodiment of the present invention. FIG. 2 corresponds to an interior structure of the light source apparatus 30 in FIG. 1.

In FIG. 2, the light source apparatus 30 includes a power supply section 31 that supplies electric power to respective sections in the light source apparatus 30, a lamp section 32 that supplies an illuminating light to the light guide of the endoscope 20, a control board 33 that includes an input/output terminal 33a that outputs a motor drive signal to a turret 34, and receives a potentiometer detection signal from the turret 34, and includes instruction means that gives an operation instruction to the turret 34 and turret control means that controls the turret 34, the turret 34 that includes an optical filter (hereinafter, sometimes simply called a filter) that transmits a light from a lamp from the lamp section 32, a motor 35 as drive means that rotationally drives the turret 34, a potentiometer 36 as a first detector that detects the rotation angle as a position of the turret 34, a lens 37 for converging an emission light, a diaphragm 38 for adjusting a light amount of the emission light, a scope insertion port 39 to which the light guide which is light guide means of an insertion portion of the endoscope (scope) is connected, and a photo reflector 40 as a second detector that detects a position in a range narrower than a range that is detected with the potentiometer 36 that is the first detector. Note that the lamp section 32 is shown in a state in which the lamp section 32 is placed by being overlaid on the power supply section 31.

Figure 3A:
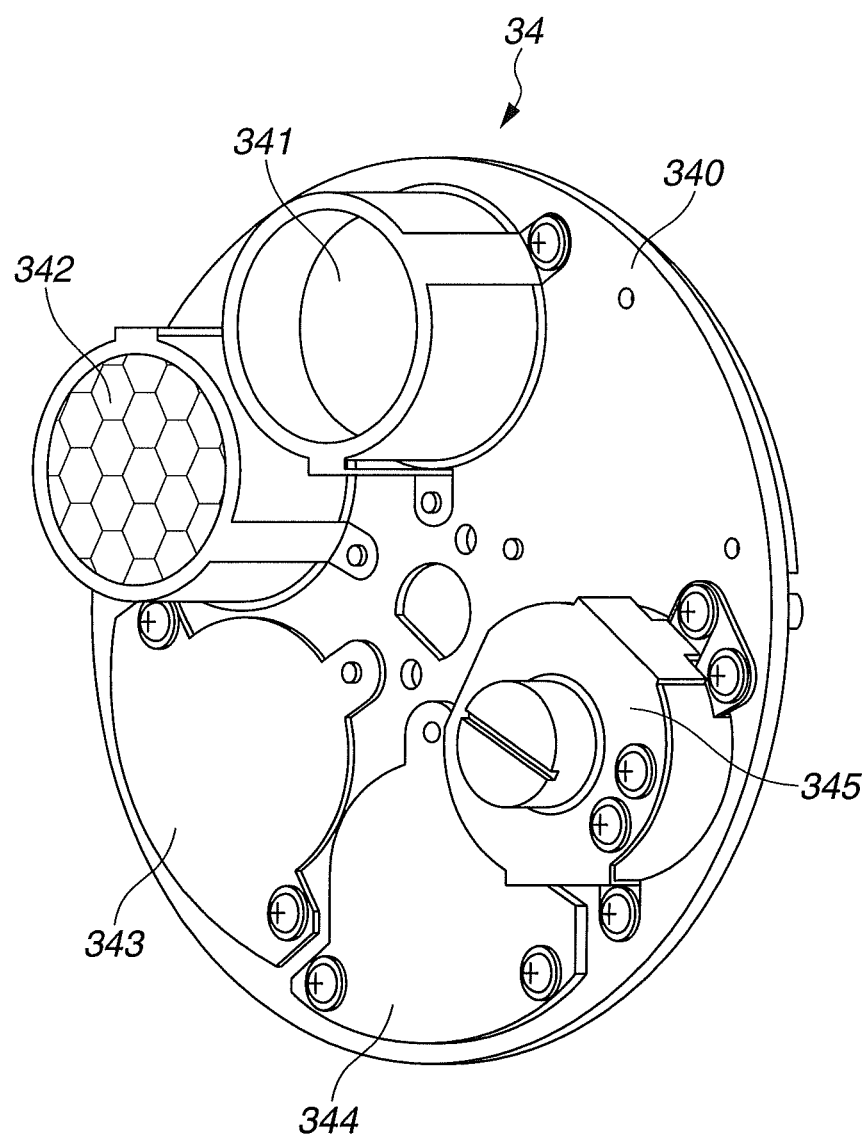
FIG. 3A is a perspective view showing a structure of a turret at an incident side.

FIG. 3A and FIG. 3B are perspective views showing a structure of the turret 34, FIG. 3A shows a perspective view of the turret 34 seen from an incident side, and FIG. 3B shows a perspective view of the turret 34 seen from an exit side respectively.

On the incident side of the turret 34, cylindrical frame bodies provided with optical filters 341 and 342 respectively are mounted to an incident side plane of a filter disk 340 with screws as shown in FIG. 3A. Further, a back surface side of an emergency light 345 is mounted to the incident side plane of the filter disk 340 with screws by using a mounting frame. Further, to the incident side plane of the filter disk 340, optical path shielding plates 343 and 344 are fastened with screws in such a manner as to close circular optical filter mounting hole portions (holes for use in the case of new optical filters being added) from the incident side, with respect to the circular optical filter mounting hole portions.

Note that if the optical filter is not installed on the turret 34, the portion corresponding thereto needs to be shielded with an optical path shielding plate as a mask. If the two optical path shielding plates 344 and 343 are not present in FIG. 3A, three regions where optical filters can be placed are vacant, and the mass balance on the filter disk 340 is lost, as a result of which, excessive load is exerted on the turret rotating motor 35, but if suitable masses are given to the optical path shielding plates 344 and 343, the mass balance can be substantially restored by the optical path shielding plates 344 and 343 being placed in the two optical filter vacant regions of the filter disk 340. Furthermore, when the optical path shielding plates 344 and 343 are removed from the state of FIG. 3A, and two of new optical filters are mounted on the two vacant optical filter regions, one of the optical path shielding plates 344 and 343 that is suitable from the viewpoint of mass out of the optical path shielding plates 344 and 343 which are removed in advance is placed on the vacant region (region where the hole is not provided) at an upper right side of FIG. 3A, whereby the mass balance can be kept more properly.

On the exit side of the turret 34, fitting portions of the optical filters 341 and 342 are mounted to an emission side plane of the filter disk 340 to be projected to some degree as shown in FIG. 3B. Further, a light emission side of the emergency light 345 is mounted to the emission side plane of the filter disk 340 to be projected with the highest height. Furthermore, it is shown that on the emission side plane of the filter disk 340, the above-described optical path shielding plates 343 and 344 block the circular optical filter mounting hole portions. In addition, on the emission side plane of the filter disk 340, six columnar detection bodies 346 the number of which is the same as the number of a plurality of (six in the drawing) optical filter regions which can be placed in a circumferential direction of an outer edge of the turret 34 are projectingly provided. The plurality of columnar detection bodies 346 are formed so that all heights thereof are the same heights, and the heights of the respective detection bodies 346 are formed to be such heights that exceed the maximum value of the heights of the plurality of projected portions which appear on the emission side of the turret 34. It is necessary that the plurality of columnar detection bodies 346 receive light from the photo reflector 40 (refer to FIG. 5) which will be described later, reflect the light on detection bodies distal end surfaces thereof, and thereby enabling the photo reflector 40 to receive the reflected light thereof and reliably perform positional detection. Accordingly, in the filter plane 340 of the turret 34, regions other than the distal end surfaces of the plurality of columnar detection bodies 346 are preferably coated with an irreflective member (for example, a black color coating material) which does not reflect the light from the photo reflector 40.

As above, the reference position of the turret is configured by the columnar detection body for each of the respective filters, and therefore, the structure can be realized, in which even if a plurality of projected portions which are projected are present on the surface of the turret, the reference positions can be reliably read with the second detector at low cost.

Figure 4:
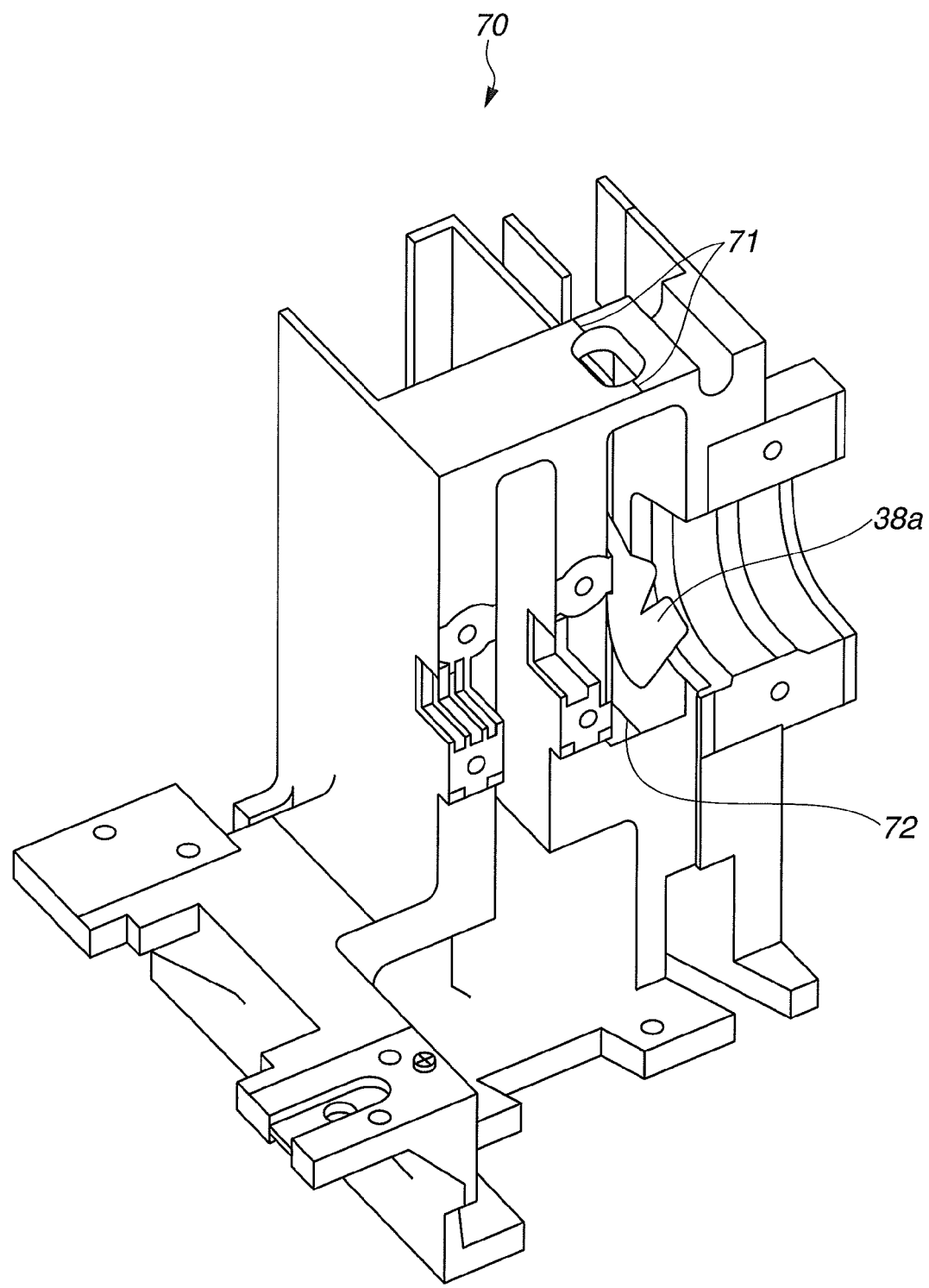
FIG. 4 is a perspective view showing a position adjustment structure that is used at a time of assembly of diaphragm blades.

FIG. 4 shows a structure which applies a measure to be able to realize enhancement of assembly precision and enhancement of assembly operability, in an assembly process of a diaphragm blade 38a as light amount control means which is placed on the light emission side of the turret 34 in the light source apparatus 30. FIG. 4 shows a configuration in which in a support body 70 that rotatably supports the diaphragm blade 38a, slits 71 and 72 are provided on a top and a bottom of a mounting portion (recessed place portion) of the diaphragm blade 38a which is formed in the support body 70, and positional adjustment of the diaphragm blade 38a is performed in correspondence with the slits 71 and 72 on the top and the bottom. The slits are provided on the top and the bottom of the mounting frame of the diaphragm blade 38a, whereby it becomes possible to determine that the positional adjustment of the diaphragm blade 38a is favorable when the slits 71 and 72 on the top and the bottom and the diaphragm blade 38a are aligned in one straight line when the slits 71 and 72 and the diaphragm blade 38a are seen from directly above. Thereby, enhancement of the assembly precision and the assembly operability of the diaphragm blade can be realized.

Figure 5:
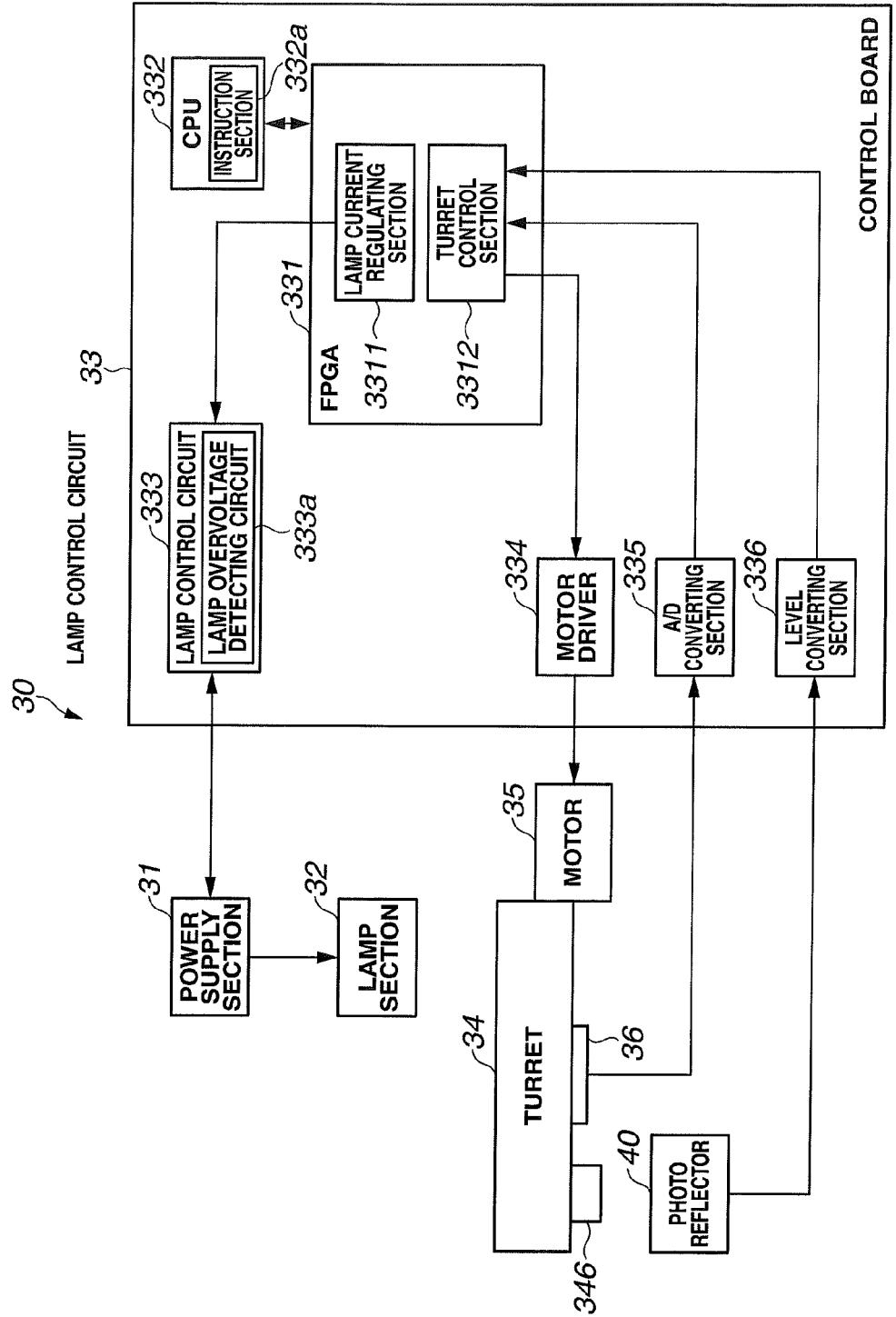
FIG. 5 is an electric control block diagram of a light source apparatus.

FIG. 5 shows an electric control block diagram of the light source apparatus 30. The same sections as the sections in FIG. 2 are assigned with the same reference signs.

In FIG. 5, the light source apparatus 30 includes the power supply section 31, the lamp section 32, the control board 33, the turret 34, the motor 35, the potentiometer 36, the detection bodies 346 and the photo reflector 40.

The potentiometer 36 is mounted to a rotary shaft of the turret 34, and an output signal thereof is sent to the control board 33. The photo reflector 40 detects the detection body 346 which is disposed at each of the optical filters, and an output signal thereof is sent to the control board 33.

An angle of the turret 34 at which the photo reflector 40 detects the detection body 346, and an angle of the turret 34 at which the optical filter enters the optical path are the same.

The detection body 346 which the photo reflector 40 detects is placed at each of the optical filters, which enters the optical path. Therefore, it is determined that for each of the optical filters, in the case of which angle, detection of the detection body 346 is performed, and the turret angles at which the six detection bodies 346 (refer to FIG. 3B) are present, that is, the angles at which the six optical filters enter the optical path increase by 60° from an angle at the time of start of rotation.

The control board 33 includes a FPGA (abbreviation of field programmable gate array) 331 including a lamp current regulating section 3311 and a turret control section 3312, a CPU 332 including an instruction section 332a as instruction means that gives an operation instruction to the turret 34, a lamp control circuit 333 including a lamp overvoltage detecting circuit 333a, a motor driver 334 of the motor 35, an A/D converting section 335 that A/D-converts a detection signal of the potentiometer 36, and a level converting section 336 that converts a level of a detection signal of the photo reflector 40.

The lamp current regulating section 3311 provided in the FPGA 331 switches an observation light mode and at the same time, switches a lamp current in the lamp current regulating section 3311 when endoscope observation is performed with an observation light of a different wavelength, whereby observation of a bright image is always enabled. For example, when a normal light observation mode by a white light (WL) and a special light observation mode by a narrow band light (NBI) are available, brightness on the monitor is very low at the time of NBI observation as compared with the WL observation. In contrast with this, the brightness on the monitor is conventionally gained by an electric gain (AGC) being increased, but noise also increases, and therefore, S/N becomes worse at the time of NBI observation. Therefore, at the time of NBI, input power (voltage, current) to the lamp is increased more than at the time of WL, whereby the brightness of the image on the monitor can be increased without noise being increased.

The turret control section 3312 provided in the FPGA 331 outputs a drive signal to the motor 35 that is drive means so as to move the turret 34 to an inside of a second range which is narrower than an inside of a first range and is detected by the photo reflector 40 that is a second detector after moving the turret 34 to the inside of the first range detected by the potentiometer 36, based on the outputs from the aforementioned instruction section 332a as the instruction means, and the potentiometer 36 that is a first detector.

As above, a drive signal of the motor 35 is controlled with the turret control signal from the turret control section 3312. A rough angle of the turret 34 is detected with the potentiometer that is the first detector, and detailed position detection of the turret 34 can be performed with the second detector, and improvement of the turret stop position precision can be realized.

The lamp control circuit 333 includes the lamp overvoltage detecting circuit 333a. The lamp overvoltage detecting circuit 333a is a circuit for turning off the lamp when a lamp of the lamp section 32 fails and is brought into a state in which an overvoltage occurs to the lamp, and turns off the lamp when the voltage exceeds a threshold value by providing the threshold value at the lamp voltage. Thereby, a patient can be prevented from getting scalded by the lamp failing to cause an excessive current of a rated current or more to flow and the lamp having an excessive light amount.

Figure 6:
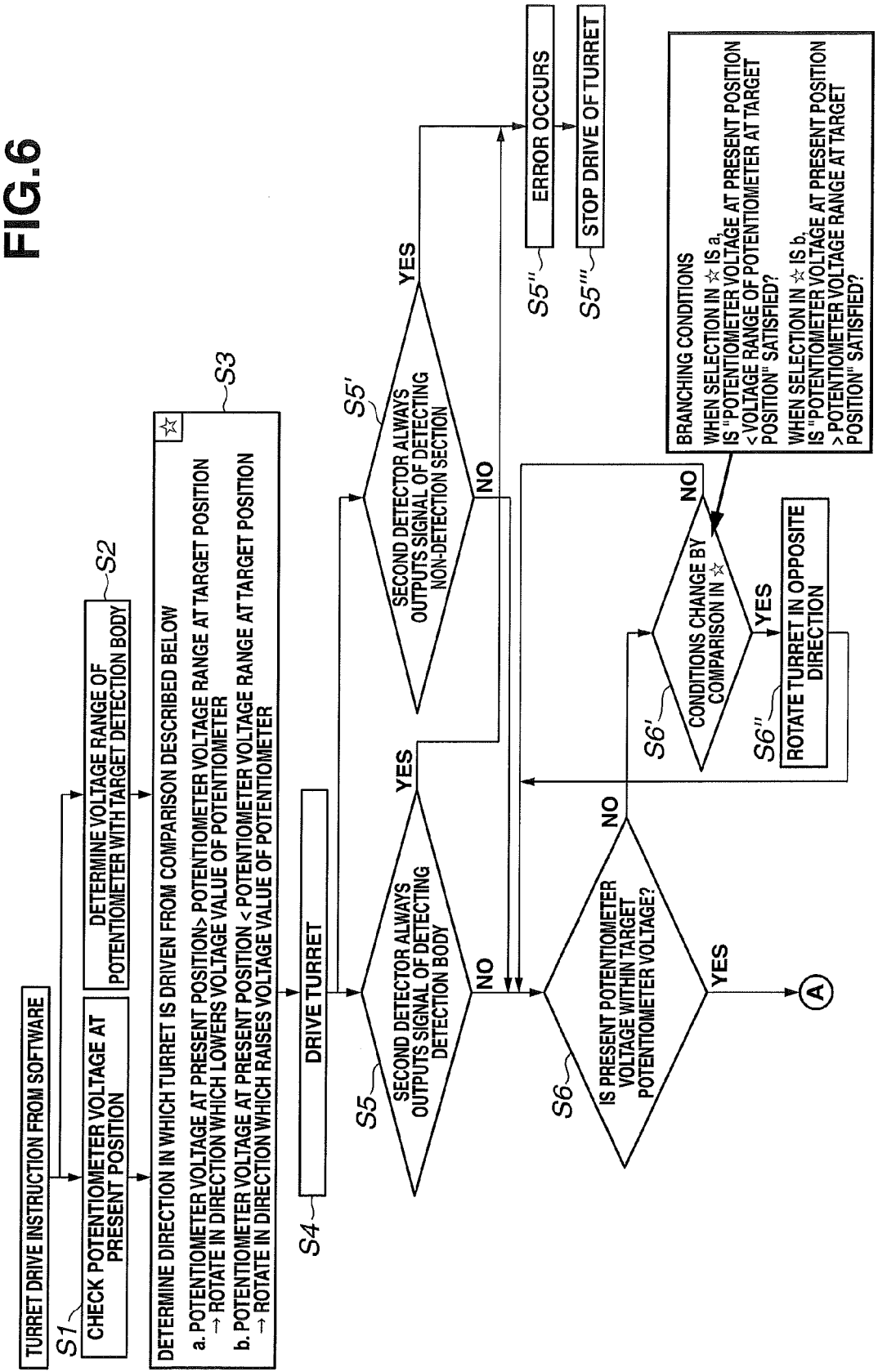
FIG. 6 is a flowchart of a control operation.
Figure 7:
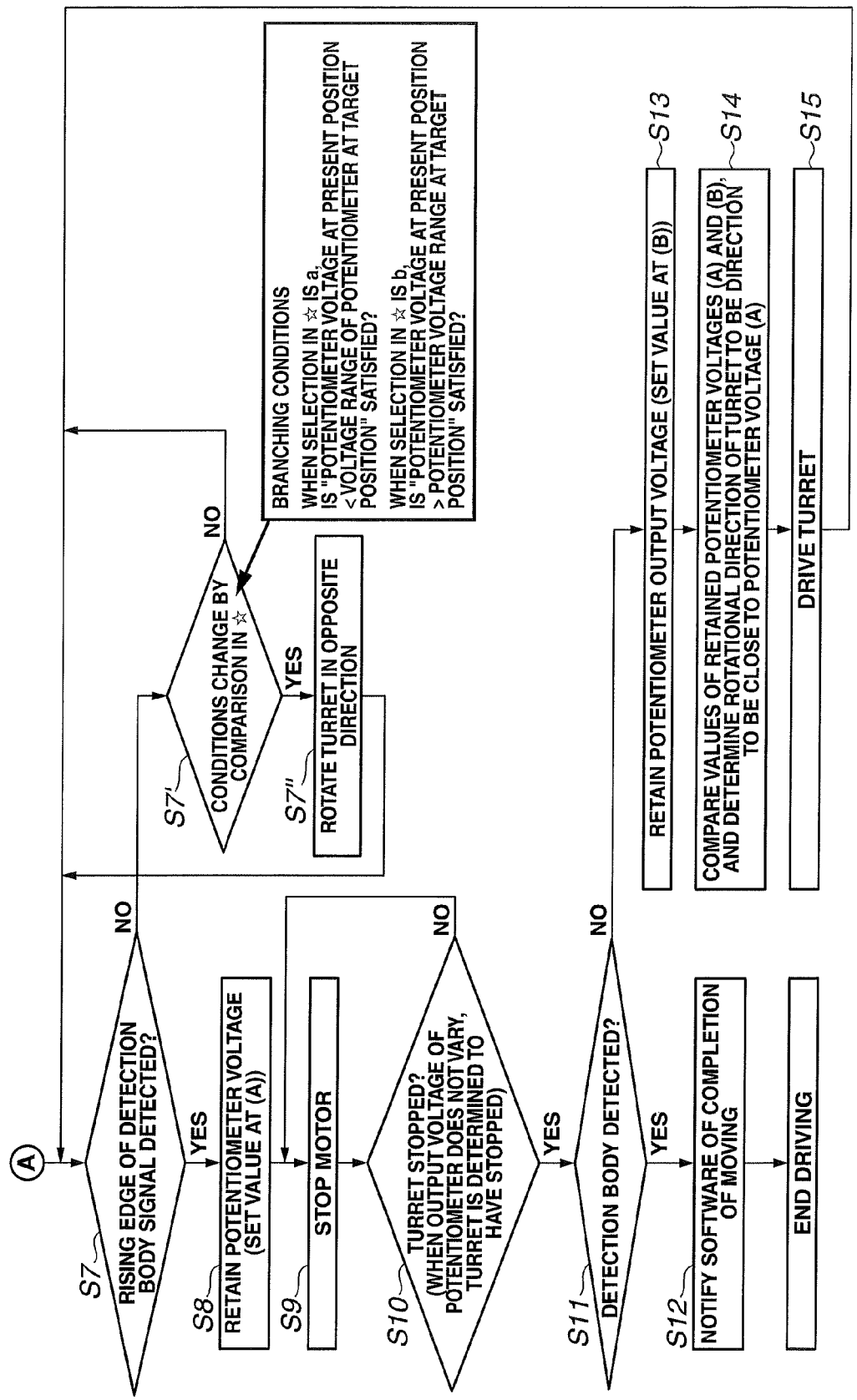
FIG. 7 is a flowchart of a control operation.

FIG. 6 and FIG. 7 are flowcharts of a control operation. Note that FIG. 6 and FIG. 7 are of one flowchart, but expressed as two diagrams because of the paper space.

A control method will be described with reference to FIG. 6 and FIG. 7.

In step S1, in the control board 33, when hardware receives a drive command of the turret 34 regarding a target position from software, the output voltage of the potentiometer 36 at the present position is detected.

In step S2, an output voltage range of the potentiometer 36 for allowing the optical filter at the target position to enter the optical path held by the hardware in advance is called.

In step S3, the results of steps S1 and S2 are obtained, the output voltage of the potentiometer 36 at the present position and the output voltage range for causing the optical filter of the target position to enter the optical path are compared with each other, and a drive direction of the motor 35 is determined.

a. Potentiometer voltage at the present position>potentiometer voltage range of the target position ⇒ rotates in the direction which lowers the voltage value of the potentiometer b. Potentiometer voltage at the present position<potentiometer voltage range of the target position ⇒ rotates in the direction which raises the voltage value of the potentiometer In step S4, the motor 35 is driven, and the turret 34 is rotated.

In step S5, it is determined whether or not the photo reflector 40 which is the second detector always outputs the signal indicating that the photo reflector 40 detects the detection body 346. Further, in step S5', it is determined whether or not the photo reflector 40 always outputs the signal indicating that the photo reflector 40 detects non-detection section (region coated with the irreflective member).

When in any one of steps S5 and S5', the signal detecting the detection body or non-detection section is always outputted, it is determined that an error occurs (step S5"), and drive of the turret 34 is stopped (step S5''').

In step S6, it is found out whether the current potentiometer output voltage is in the target potentiometer output voltage range.

When the current potentiometer output voltage is within the target voltage range, the flow proceeds to step S7.

When the current potentiometer output voltage is outside the target voltage range, the flow proceeds to step S6', and from the comparison result in step S3, it is determined whether the turret 34 is rotated as it is, or rotated in the opposite direction.

When the comparison result in step S3 is a, the turret 34 is rotated in a direction which lowers the potentiometer voltage, but when "potentiometer voltage at the present position<the potentiometer voltage range of the target position" is satisfied, the turret 34 is excessively rotated, and therefore, the turret 34 is rotated in the opposite direction as shown in step S6." Otherwise, the turret 34 is rotated as it is.

When the comparison result in step S3 is b, the turret 34 is rotated in a direction which raises the potentiometer voltage, but when "potentiometer voltage at the present position>potentiometer voltage range of the target position" is satisfied, the turret is excessively rotated, and therefore, the turret is rotated in the opposite direction as shown in step S6." Otherwise, the turret is rotated as it is.

In step S7, in order to find out that the photo reflector 40 detects the detection body 346, a rising edge of a photo reflector output signal at a time of the detection body 346 being detected is detected.

When the rising edge is detected, the flow proceeds to step S8.

When the rising edge is not detected, the flow proceeds to step S7', and from the comparison result in step S3, it is determined whether the turret 34 is rotated as it is, or rotated in the opposite direction.

When the comparison result in step S3 is a, the turret 34 is rotated in the direction which lowers the potentiometer voltage, but when "potentiometer voltage at the present position<potentiometer voltage range of the target position" is satisfied, the detection body 346 is not detected, and therefore, the turret 34 is rotated in the opposite direction as shown in step S7," whereby detection of the detection body 346 is performed. Otherwise, the turret 34 is rotated as it is, and detection of the detection body 346 is continued.

When the comparison result in step S3 is b, the turret 34 is rotated in the direction which raises the potentiometer voltage, but when "potentiometer voltage at the present position>potentiometer voltage range of the target position" is satisfied, the detection body 346 is not detected, and therefore, the turret is rotated in the opposite direction as shown in step S7," whereby detection of the detection body 346 is performed. Otherwise, the turret 34 is rotated as it is, and detection of the detection body 346 is continued.

In step S8, the output voltage value of the potentiometer 34 at the time of the rising edge of the photo reflector output signal being detected is retained. The retained value is set as (A).

In step S9, a control signal that stops the motor 35 is sent.

In step S10, even after the control signal that stops the motor 5 is sent, the turret 34 also rotates as the motor 5 rotates by inertia, and therefore, in order to find out that rotation of the turret 34 completely stops, it is found out that there is no variation of the output voltage value of the potentiometer 36.

In step S11, there is the possibility that the photo reflector 40 does not detect the detection body 346 due to the influence of the rotation by the inertia of the motor 34 of step S10 when the rotation of the turret 34 stops, and therefore, it is ascertained that the photo reflector 40 detects the detection body 346.

When the photo reflector 40 detects the detection body 346, the flow proceeds to step S12.

When the photo reflector 40 does not detect the detection body 346, the flow proceeds to step S13, the potentiometer output voltage at the time is retained, and a value thereof is set as (B).

The potentiometer output voltage (A) retained in step S8 and the current potentiometer output voltage (B) are compared, and if the current potentiometer output voltage overruns, the rotational direction of the turret is determined to be the direction to approach the potentiometer output voltage value (A) (step S14). The turret 34 is rotationally driven in step S15.

In step S12, the drive of the turret 34 is completed, and therefore, the software is notified of the completion of the movement, and the drive of the turret 34 is completed.

Note that the second detector may be an optical sensor such as a photo interrupter, besides the photo reflector 40. In the case of the photo interrupter, drive of the motor 35 can be stopped when a matter which blocks the optical path between the LED and the sensor enters.

The detection body 346 may be either a reflective body or an irreflective body, and the user can make choice.

When the photo reflector 40 is used, a sheet metal portion with a high reflectivity and a silk portion with a low reflectivity are inverted and an area of the silk portion is made large, so that the LED light emission of the photo reflector does not become disturbance noise to other photo reflectors, whereby the influence of the disturbance noise is suppressed.

According to the first embodiment, when control of the rotation angle of the turret is performed, the rough angle is detected with the potentiometer that is the first detector, and the detailed positional detection can be performed with the second detector. The detailed positional detection of the rotation angle is performed at the position apart from a center, whereby detection with higher precision than a substantially center of the turret can be performed even when the detection precision is equivalent. Furthermore, when the rotation control of the turret is to be performed with only the second detector, the second detectors the number of which corresponds to the number of the detection positions are required in the outer circumferential direction of the turret, the cost increases and the size also increases, whereas in the present first embodiment, by combination with the first detector, improvement of the turret stop position precision is realized, and the stop precision of the turret can be enhanced at low cost with a relatively simple system.

Second Embodiment

Figure 8:
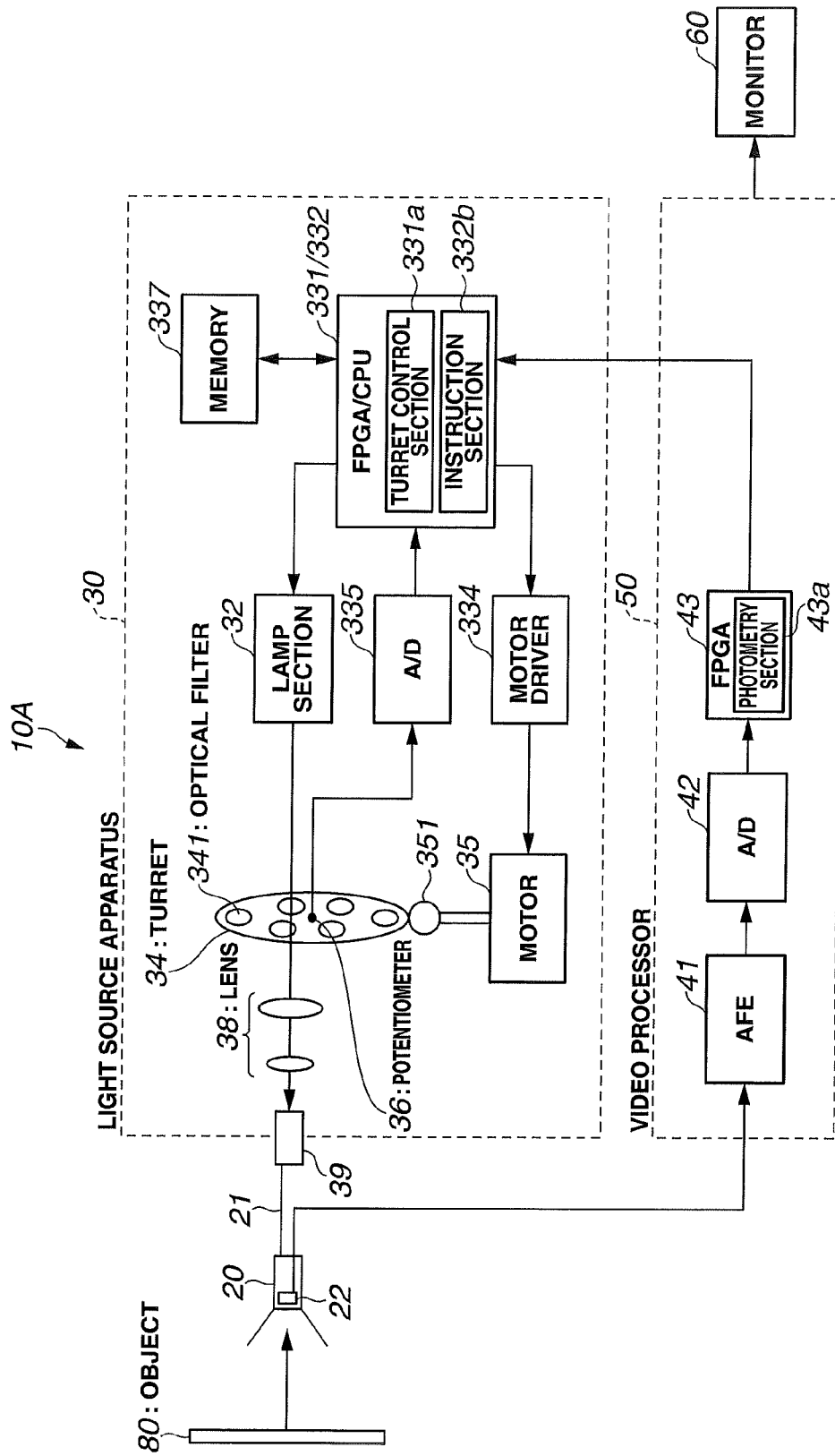
FIG. 8 is a block diagram showing an endoscope system of a second embodiment of the present invention.

FIG. 8 is a diagram showing an endoscope system of a second embodiment of the present invention.

In FIG. 8, an endoscope system 10A includes the endoscope 20 including the light guide 21 as light guide means that guides an illuminating light to the distal end portion and the CCD 22 as the image pickup device that picks up an image of a reflected light image from an object 80, the light source apparatus 30 that emits light to the light guide 21 that guides the illuminating light to the endoscope distal end portion, the video processor 50 which performs signal processing of an endoscopic image picked up with the CCD 22 at the endoscope distal end portion, the monitor 60 that displays the endoscopic image which is subjected to signal processing, and a power supply section (not illustrated). In the second embodiment of FIG. 8, the second detector shown in the first embodiment is not required.

The light source apparatus 30 includes the FPGA 331 and the CPU 332, the lamp section 32, the turret 34 including the optical filter 341, the motor 35 as the drive means including a gear 351, the potentiometer 36 as the detector that detects the position of the turret 34, the motor driver 334 that drives the motor 35, the A/D convertor 335 that A/D-converts the output of the potentiometer 36, a memory 337 as storage means that stores information for driving the turret 34, and the scope insertion port 39.

The above described FPGA 331 and CPU 332 include an instruction section 332b as instruction means that performs instruction to cause the memory 337 to store information for driving the turret 34, and a turret control section 331a as turret control means that outputs a drive signal for causing the turret 34 to make one rotation to the motor 35 and stores a detection value from the potentiometer 36 at which a measured value from a photometry section 43a as photometry means becomes a maximum value while the turret 34 makes one rotation, into the memory 337 by the instruction of the instruction section 33b.

The video processor 50 includes a preamplifier 41, an A/D convertor 42, and an FPGA 43 including the photometry section 43a as the photometry means that generates a photometric signal from the image pickup signal from the CCD 22 and outputs the photometric signal. The photometry section 43a in the FPGA 43 calculates a level of brightness (light output intensity) received by the CCD 22, and outputs the level of the brightness to the FPGA 331 and the CPU 332 in the light source apparatus 30.

In the above-described configuration, an output voltage of the potentiometer 36 and the level of the brightness received by the CCD 22 are associated with each other, and a potentiometer voltage at which a brightness peak is present is used as a positioning target value (reference) of the turret 34.

For association, adjustment steps 1 to 6 as follows are required.

1: The light source apparatus 30, the video processor 50, and a white chart as the object 80 are prepared, and the lamp is lit.

2: The turret 34 is rotated at a desired rotational speed from a certain position until all the filters pass through the optical axis (rotation is optional, such as one rotation, a plurality of rotations, and a reverse rotation).

3: The output voltage of the potentiometer 36 at the time of the state of 2 is read, and is taken into the FPGA 331/CPU 332.

3': CCD output which is the result of receiving a reflected light from the white chart at the time of the state of 2 is taken into the FPGA 331/CPU 332 of the light source apparatus 30 as brightness information via the video processor 50.

4: The relation of the potentiometer output voltage and the brightness information can be calculated from 3 and 3'.

5: If six optical filters are present, the output of the CCD 22 has six brightness peaks, and therefore, the output voltages at the time of output thereof are referred to and stored in the memory 332.

6: The stored voltages are used as a stop angle reference of the turret 34, and drive control of the turret 34 is performed with the control method similar to the conventional control method.

Note that the present adjustment steps can be performed during inspection (aging of the lamp and the turret) of the light source apparatus 30, for example, and therefore, the number of adjustment process steps is not required additionally.

Having the brightness peak means that the filter of the turret comes to the optical axis, and therefore, becomes the reference for positional control.

In place of the CCD, an optical sensor, a power meter or the like may be used.

The peak detection method may be a method which causes the turret to make a plurality of rotations and takes an average value of the number of plurality of rotations and the like, besides the method for taking the peak when the turret makes one rotation.

Figure 9:
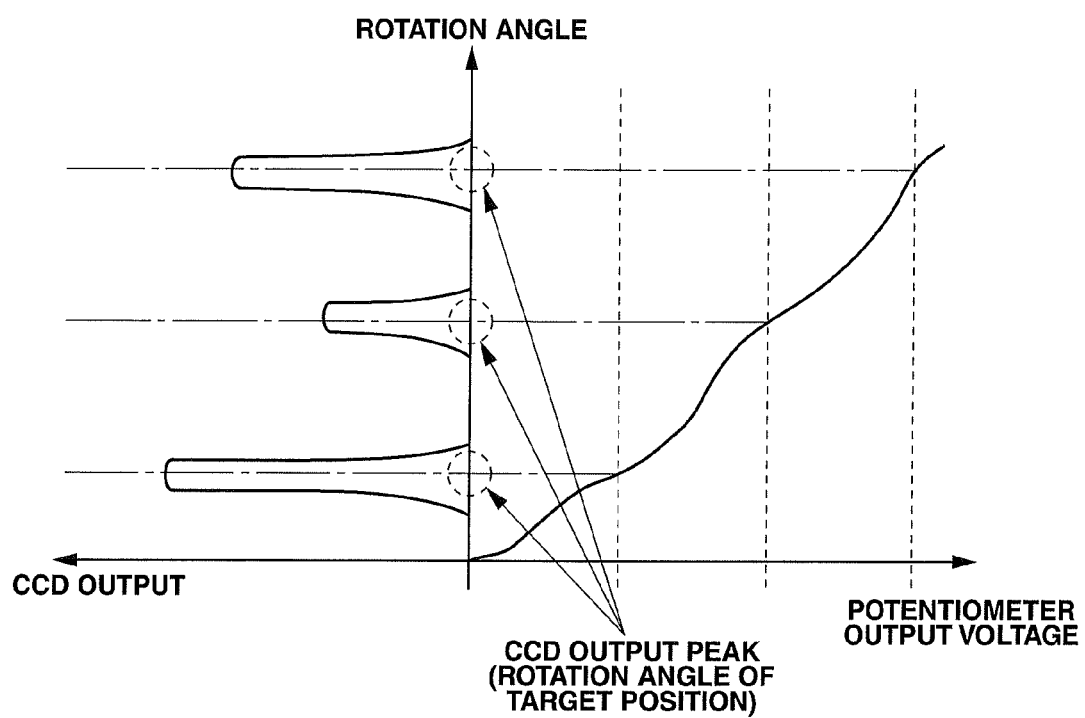
FIG. 9 is a diagram showing a relation of a CCD signal output, a turret rotational angle and a potentiometer voltage.

FIG. 9 is a diagram showing a relation of the CCD signal output, the turret rotation angle and the potentiometer voltage. Before shipment or before use of the light source apparatuses, the potentiometer voltages corresponding to the CCD output peaks (turret rotation angles) are measured and stored in advance in the memory 337 individually for the actual light source apparatuses.

According to the second embodiment, the stop precision of the turret can be enhanced without adoption of a potentiometer with high precision or increase of mechanical precision, and without increase of cost with the light source apparatus and the configuration of the turret in the conventional art being kept.

The present invention is not limited to the embodiments described above, and various modifications, alterations and the like can be made within the range without departing from the gist of the present invention.

What is claimed is:

1. An endoscope light source apparatus, comprising:
    a turret provided to be rotatable about a predetermined axis, and provided with a first optical filter and a second optical filter for transmitting an illuminating light on a circumference of the rotation;
    an instruction section in which an operation instruction is inputted, the operation instruction being for locating and stopping the first optical filter or the second optical filter provided to the turret on an optical path of the illuminating light;
    a drive section that rotationally drives the turret;
    a first detector that detects a rotation angle of the turret and outputs a detection signal according to a result of the detection;
    a first detected portion for identifying a position of the first optical filter;
    a second detected portion for identifying a position of the second optical filter;
    a second detector that optically detects a position of the first or the second detected portion; and
    a turret control section that outputs a drive signal to the drive section to move the turret until the first or the second detected portion is detected by the second detector in order to position the optical filter designated in response to an input of the instruction section, after moving the turret so that a value of the detection signal detected by the first detector falls within a range set in advance, in response to the input of the instruction section, and stop the turret in response to the first or the second detected portion being detected.

2. The endoscope light source apparatus according to claim 1, wherein the second detector detects a position of a mark provided in a circumferential direction of an outer edge of the turret.

3. The endoscope light source apparatus according to claim 2,
    wherein the second detector detects an optical reflected light, and
    a columnar detected portion exceeding a maximum value of heights of a plurality of projection portions included in the turret is provided, and the detected portion is detected by the second detector.

4. The endoscope light source apparatus according to claim 1,
    wherein the second detector detects an optical reflected light, and
    a columnar detected portion exceeding a maximum value of heights of a plurality of projection portions included in the turret is provided, and the detected portion is detected by the second detector.

5. The endoscope light source apparatus according to claim 4, wherein sections other than the columnar detected portion in the turret are covered with an optical irreflective member.

6. The endoscope light source apparatus according to claim 4, wherein as many of the columnar detected portions as a number of optical filter regions, a plurality of which can be placed in a circumferential direction of an outer edge of a filter disk of the turret, are projectingly provided on the filter disk.

* * * * *